United States Patent

Hall et al.

[11] Patent Number: 4,783,473
[45] Date of Patent: Nov. 8, 1988

[54] GEMINALLY SUBSTITUTED CYCLIC ETHER CARBOXYLIC ACIDS, DERIVATIVES THEREOF, COMPOSITIONS CONTAINING SAME AND METHOD OF USE

[75] Inventors: Steven E. Hall, Ewing Township, Mercer Co.; Philip M. Sher, Plainsboro, both of N.J.

[73] Assignee: E. R. Squibb & Sons, Inc., Princeton, N.J.

[21] Appl. No.: 92,247

[22] Filed: Sep. 2, 1987

[51] Int. Cl.$^4$ .................. A61K 31/34; A61K 31/35; C07D 307/16; C07D 309/06

[52] U.S. Cl. .................. 514/382; 514/451; 514/459; 514/461; 514/471; 548/252; 548/253; 549/426; 549/427; 549/491; 549/496; 549/499; 549/500; 549/501

[58] Field of Search .............. 548/252, 253; 549/426, 549/427, 491, 496, 499, 500, 501; 514/451, 459, 461, 471, 382

[56] References Cited

U.S. PATENT DOCUMENTS 4,258,058  3/1981  Witte et al. .................. 424/309
4,443,477  4/1984  Witte et al. .................. 424/319

OTHER PUBLICATIONS

Derwent 87-058524/09 (Sano 30.08.85).
Derwent 86-101869/16 (Sano 10.10.84).
Derwent 85-147824 (Meri 14.11.83).
Derwent 85-232492/38 (Fuji 12/01/84).
Derwent 85-220819/36 (Fuji 28.12.83).

*Primary Examiner*—Richard L. Raymond
*Attorney, Agent, or Firm*—Lawrence S. Levinson; Burton Rodney

[57] ABSTRACT

Geminally-substituted cyclic ether carboxylic acids or derivatives thereof are provided which have the structure

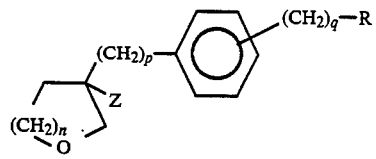

wherein Z is aryl, which may be optionally substituted with one or more of the following groups: halo, lower alkyl, lower alkoxy, hydroxy, lower alkylamino, phenyl or carbo-lower alkoxy

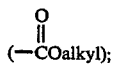

R is COOH, COO alkali metal, coo lower alkyl,

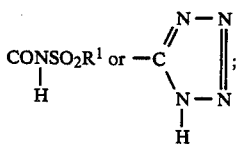

$R^1$ is lower alkyl or aryl;
n is 1 or 2;
p is 2 to 5; and
q is 1 to 4.

These compounds are cardiovascular agents which exhibit thromboxane antagonist activity and thus are useful in the treatment of thrombotic disease.

13 Claims, No Drawings

GEMINALLY SUBSTITUTED CYCLIC ETHER CARBOXYLIC ACIDS, DERIVATIVES THEREOF, COMPOSITIONS CONTAINING SAME AND METHOD OF USE

FIELD OF THE INVENTION

The present invention relates to geminally substituted cyclic ether carboxylic acids and derivatives thereof which are useful in the treatment of thrombotic disease.

BACKGROUND OF THE INVENTION

U.S. Pat. No. 4,258,058 to Witte et al discloses phenoxyalkyl carboxylic acids which inhibit thrombocyte aggregation and depress serum lipids and have the structure

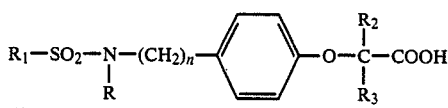

wherein

R is hydrogen or lower alkyl;

$R_1$ is an alkyl or aryl, aralkyl or aralkenyl radical, the aryl moiety of which can be substituted one or more times by halogen, hydroxyl, trifluoromethyl or lower alkyl, alkoxy or acyl;

$R_2$ and $R_3$, which can be the same or different, are hydrogen or lower alkyl and n is 0, 1, 2, or 3;

as well as the physiologically acceptable salts, esters and amides thereof.

U.S. Pat. No. 4,443,477 to Witte et al discloses sulphonamidophenyl carboxylic acids which inhibit thrombocyte aggregation and depress serum lipids and have the structure

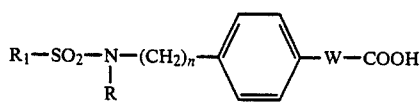

wherein

R is a hydrogen atom or a lower alkyl radical;

$R_1$ is an alkyl radical or an aryl, aralkyl or aralkenyl radical, the aryl moiety of which in each case can be optionally substituted one or more times by hydroxyl, halogen, trifluoromethyl, lower alkyl or alkoxy or by acyl, carboxy or alkoxycarbonyl;

n is 1, 2 or 3; and

W is a bond or an unbranched or branched divalent aliphatic hydrocarbon chain, which is either saturated or contains a double bond, as well as the physiologically acceptable salts, esters and amides thereof.

DESCRIPTION OF THE INVENTION

In accordance with the present invention, geminally-substituted cyclic ether carboxylic acid compounds or derivatives thereof are provided having the following structural formula:

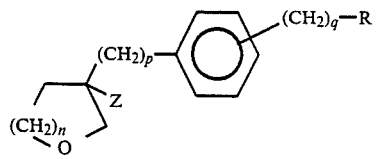

wherein

Z is aryl which may be optionally substituted with one or more of the following groups: halo, lower alkyl, lower alkoxy, hydroxy, lower alkylamino, phenyl or carbo-lower alkoxy

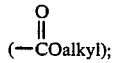

R is COOH, COO-alkali metal (such as Na, K or Li), COO-lower alkyl, $CONHSO_2R^1$ or 5-tetrazolyl;

$R^1$ is lower alkyl or aryl;

n is 1 or 2;

p is 2 to 5; and q is 1 to 4.

The $(CH_2)_n$, $(CH_2)_p$ and $(CH_2)_q$ groups may be optionally substituted with one or two lower alkyl and/or one or two lower alkoxy substituents.

The $-(CH_2)_q-R$ group may be attached at the ortho, meta or para position, with para being preferred.

Thus, the compounds of the invention include the following types of compounds.

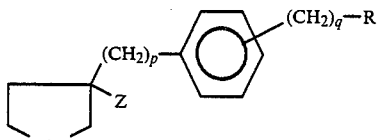

and

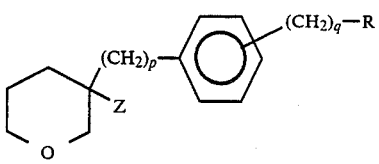

The term "lower alkyl" or "alkyl" as employed herein by itself or as part of another group includes both straight and branched chain hydrocarbon radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including one or two halo-substituents, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), and/or 1 or 2 lower alkoxy groups.

The term "aralkyl", "aryl-alkyl" or "aryl-lower alkyl" as used herein by itself or as part of another group refers to lower alkyl groups as discussed above having an aryl substituent, such as benzyl.

The term "lower alkoxy" refers to a lower alkyl group linked to an oxygen.

The term "lower alkylamino" refers to a lower alkyl group linked to —NH—.

The term "halogen" or "halo" as used herein by itself or as part of another group refers to chlorine, bromine, fluorine, iodine or $CF_3$, with chlorine being preferred.

The terms "$(CH_2)_n$", "$(CH_2)_p$" and "$(CH_2)_q$" where present include a straight or branched chain radical having 1 or 2 carbons in the normal chain in the case of "$(CH_2)_n$", 2 to 5 carbons in the normal chain in the case of "$(CH_2)_p$" and 1 to 4 carbons in the normal chain in the case of "$(CH_2)_q$" and may contain one or more lower alkyl and/or lower alkoxy substitutents. Examples of $(CH_2)_n$, $(CH_2)_p$ and $(CH_2)_q$ groups include

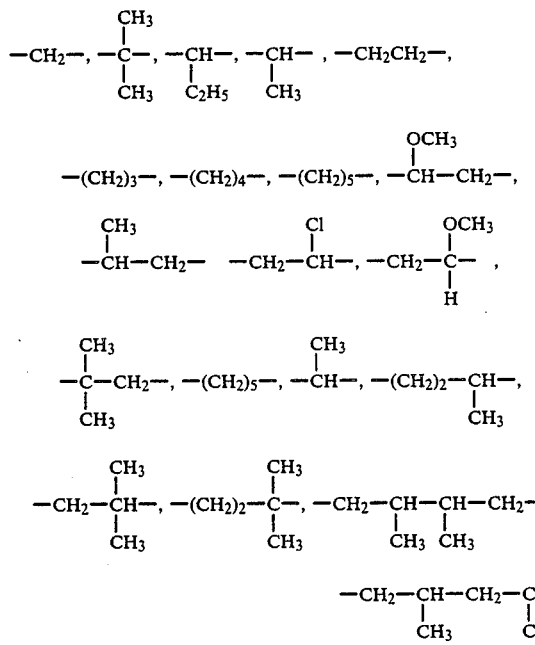

and the like.

Preferred are those compounds of the invention wherein Z is phenyl or halophenyl, such as p—Cl—C$_6$H$_4$—, n is 1, $(CH_2)_p$ is $(CH_2)_3$, $(CH_2)_q$ is —CH$_2$—and is in the para position on the benzene ring and R is COOH.

The various compounds of the invention may be prepared as outlined below.

Compounds of formula I of the invention wherein R is other than 5-tetrazolyl may be prepared starting with the protected lactone compound II

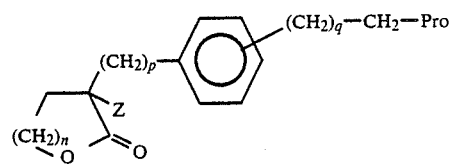

where Pro represents a protected alcohol group such as

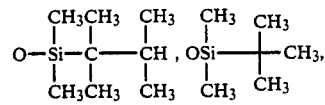

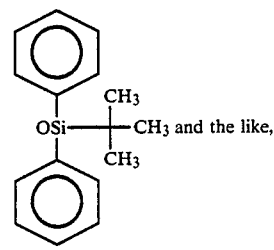

which is reduced by treating lactone II with a reducing agent such a lithium aluminum hydride of lithium borohydride, in the presence of an organic solvent such as ethyl ether, or tetrahydrofuran, under an inert atmosphere such as argon, at a temperature of within the range of from about −20° to about 40° C. to form the protected open chain compound III

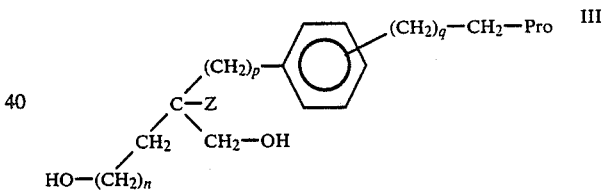

Compound III is then subjected to a ring closure reaction by treating III with an activating agent such as p-toluenesulfonyl chloride, or methane sulfonyl chloride in the presence of an organic amine such as triethylamine, tributylamine or pyridine in an organic solvent such as methylene chloride, ethyl ether or tetrahydrofuran under an inert atmosphere such as argon, to form the cyclic ether IV

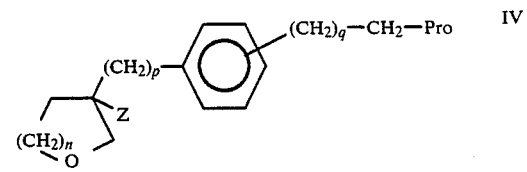

Cyclic ether IV is treated with Jones Reagent (that is, CrO$_3$ dissolved or suspended in concentrated sulfuric acid) in the presence of an organic solvent such as acetone, at a temperature of within the range of from about −20° to about 20° C., to remove the protecting group and oxidize to form the cyclic ether of the invention IC

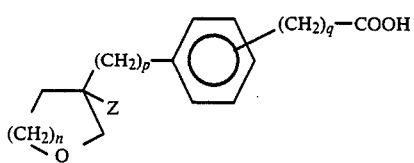

Compounds of the invention wherein R is COO-alkyl, that is, ID

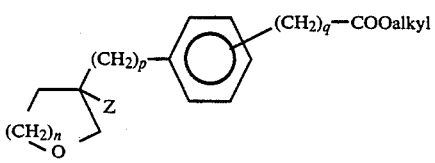

may be prepared by subjecting IC to esterification by reacting IC with an alcohol V alkyl—OH V employing conventional esterification procedures.

Compounds of the invention wherein R is COO-alkali metal may be prepared by subjecting ester ID to hydrolysis by treating ID with an alkali metal hydroxide such as NaOH, KOH or LiOH, in the presence of an inert organic solvent such as tetrahydrofuran, methanol or dimethoxyethane, to form the corresponding alkali metal salt IE

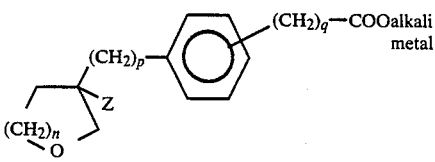

Salt IE may then be treated with strong acid such as hydrochloric acid to form the acid compound IC.

Compound of formula I of the invention wherein R $$\begin{matrix} CONSO_2R^1 \\ | \\ H \end{matrix}$$

may be prepared by subjecting acid IC to a coupling reaction by reacting acid IC with a coupling agent, for example, dicyclohexylcarbodiimide or 1,1'-carbonyldiimidazole and reacting this intermediate with a sulfonamide VI $H_2NSO_2R^1$  VI Compounds of formula I of the invention wherein R is 5-tetrazolyl may be prepared as described above except starting with the lactone IIA

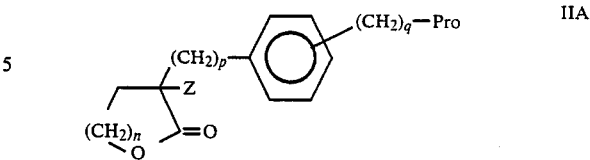

Lactone IIA is reduced, as described above with respect to lactone II, to form the open chain compound IIIA

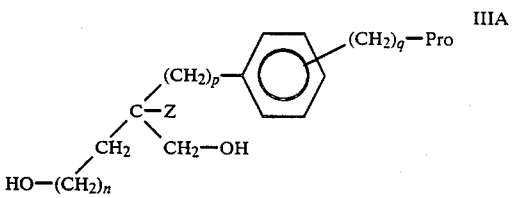

which is subjected to a ring closure reaction, as described with respect to open chain compound III, to form the cyclic ether IVA

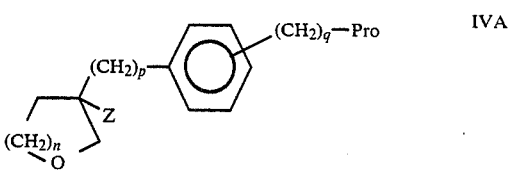

Cyclic ether IVa is subjected to conventional deprotecting procedures, for example, treating with mild aqueous acid, to form the alcohol VII

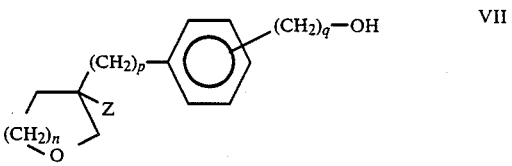

which is activated by conversion, for example to the bromide by treatment with triphenylphosphine and bromine to form the bromide compound VIII

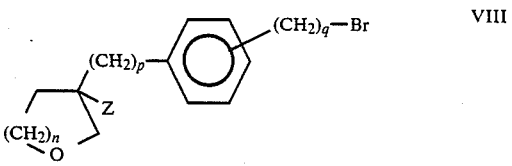

Bromide VIII is treated with inorganic cyanide such as NaCN or KCN to form the corresponding cyanide compound IX

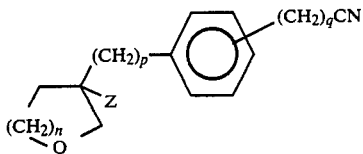

which is subjected to a cycloaddition reaction by treating IX with sodium azide or lithium azide in the presence of a polar solvent such as dimethylformamide to form the tetrazole IF

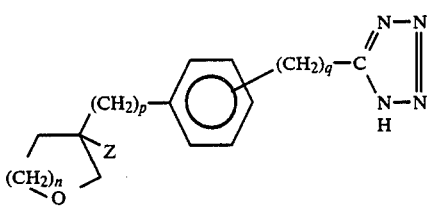

The starting material II may be prepared by alkylation of lactone X

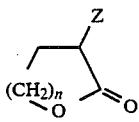

by treating X with a protected aralkylhalide XI

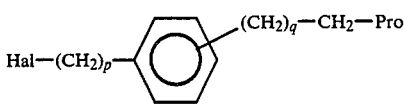

in the presence of a strong base such as lithium di(isopropyl) amide or lithium bis(trimethylsilyl)amide. In carrying out the above reaction, the lactone X is employed in a molar ratio to the halide XI of within the range of from about 2:1 to about 0.5:1. The reaction is carried out at a temperature of within the range of from about −78° to about 25° C. for a period of from about 2 to about 20 hours.

The starting material XI may be prepared starting with protected aryl halide compound XII

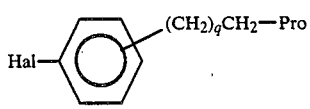

which is added to a mixture of magnesium and I₂ in an inert organic solvent such as tetrahydrofuran under an inert atmosphere such as argon to form a Grignard solution. The Grignard solution is added to a stirred solution of dihaloalkane XIII

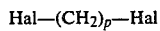

and Li₂CuCl₄ in the presence of an inert organic solvent such as tetrahydrofuran and under an inert atmosphere such as argon to form XI.

The starting material IIA may be prepared by the procedure described above for II, except employing bromide XIV instead of bromide XI.

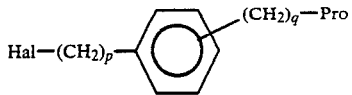

The lactone X may be prepared by treating a substituted acetonitrile XV

with a strong base such as lithium bis(trimethylsilyl) amide or lithium diisopropyl amide and ethylene oxide or trimethylene oxide optionally in the presence of a Lewis acid such as BF₃·Et₂O and treating that reaction mixture with strong acid such as hydrochloric acid or hydrobromic acid in the presence of ethanol and water.

In carrying out the above reaction, the substituted acetonitrile XV will be employed in a molar ratio to the ethylene oxide of within the range of from about 1:1 to about 0.1:1. The reaction will be carried out at a temperature of within the range of from about −78° to about 25° C. for a period of from about 2 to about 20 hours.

The compounds of this invention are cardiovascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are also thromboxane A₂ receptor antagonists, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc., as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

4-[3-(Tetrahydro-3-phenyl-3-furanyl)propyl]benzeneacetic acid

A.
3-(4-(2-(Thexyldimethylsilyloxy)ethyl)-phenyl)propyl bromide

To a stirred mixture of Mg (7.00 g, 0.29 mol) and I2 (one crystal) in 70 ml of dry THF under argon at 30° C. was added dropwise 10% of a solution of p-(2-(thexyldimethylsilyloxy)ethyl)phenyl bromide (50 g, 0.14 mol) in 10 ml of dry THF. This mixture was stirred vigorously and the I2 color disappeared in 5 minutes. The remaining THF solution of bromide was added dropwise over 15 minutes. The mixture was heated at 40° C. for one hour and cooled to room temperature. To a stirred solution of 1,3-dibromopropane (18 ml, 0.18 mol) and 0.1M solution of Li2CuCl4 in THF (28 ml, 2.8 mmol) in 50 ml of dry THF under argon at 0° C. was added the above Grignard solution at a rate such that the pot temperature did not exceed 7° C. An additional 110 ml of dry THF was used to rinse in the residue of the Grignard reagent. The addition on this scale took 70 minutes. The reaction mixture was stirred at 0° C. for one hour and 2 hours at room temperature. The reaction mixture was cooled to 0° C. and quenched by dropwise addition of 30 ml of CH3OH over 5 minutes. The mixture was concentrated in vacuo and partitioned between saturated NH4Cl solution (800 ml) and ether (3×800 ml). The combined ether extracts were dried (MgSO4), filtered and concentrated in vacuo. The crude product was subjected to bulb to bulb distillation under vacuum to give 37.8 g (68%) of title bromide. TLC: silica gel, hexane-benzene 1:1, $R_f$ 0.86, Ce(SO4)2.

B.
3-[4-[2-(Thexyldimethylsilyloxy)ethyl]-phenyl]propyl iodide

To a solution of 9.3 g of impure 3-(4-(2-(thexyldimethylsilyloxy)ethyl)pnenyl)propyl bromide (<24 mmol) in 30 ml acetone (which had been dried by stirring over K2CO3) was added 0.1 g NaHCO3 and 19.7 g NaI (131 mmol). The mixture was stirred in the dark at room temperature overnight. Water and 3 M aqueous NaHSO3 solution were added, and the mixture was extracted with CH2Cl2 three times. The combined extracts were dried over Na2SO4 and evaporated. Trace moisture was removed azeotropically by rotoevaporation with toluene (twice), then hexane (twice). Exposure to high vacuum gave 10.2 g of impure title iodide as an oil. The yield of title iodide was approximately 97%.
TLC (2% EtOAc in hexanes - anisaldehyde):
  Part A bromide 0.27
  Title iodide 0.27

C.
2-Phenyl-2-[3-[4-[2-(thexyldimethylsilyloxy)ethyl]-phenyl]propyl]-γ-butyrolactone To a solution of 8.9 ml of 1M lithium bis(trimethylsilyl)amide in THF solution (8.9 mmol, 1.2 equiv) diluted with 10 ml dry THF, stirring at −78° under argon, was added dropwise a solution of 1.20 g of α-phenyl-γ-butyrolactone (7.4 mmol, prepared from diethyl phenylmalonate according to H. Y. Aboul-Enein and E. A. Lotfi, *Indian J. Chem.*, 1980, 19B, 1083) in 9 ml of dry THF. After stirring 1 hour, a solution of 4.5 g of impure Part B iodide (<10.4 mmol, <1.4 equiv) in 10 ml dry THF was added dropwise. After 1 hour of stirring at −78° in the dark, the mixture was allowed to slowly warm to room temperature. Stirring was continued at room temperature overnight. Addition of 1 ml saturated aqueous NH4Cl solution caused precipitation. The precipitate was filtered off, washing with THF, and the filtrate was concentrated. The residue was flash chromatographed (0% to 15% EtOAc in hexanes gradient) to obtain 2.71 g of nearly pure title alkylation product as an oil. The yield of title alkylation product was 78%.
TLC 15% EtOAc in hexanes - I2, UVS):
  Part B iodide: 0.84
  α-phenyl-γ-butyrolactone: 0.08
  title alkylation product: 0.33

D.
3-Hydroxymethyl-3-phenyl-6-[4-[2-(thexyldimethylsilyloxy)ethyl]phenyl]-hexan-1-ol To a solution of 1.49 g of Part C lactone (3.2 mmol) in 15 ml dry ether stirring under argon at 0°, was added 1.1 g lithium aluminum hydride (29 mmol, 9.0 equiv.). The mixture was then warmed to room temperature and stirred overnight. After recooling to 0°, 20% EtOAc in Et2O was cautiously added to quench excess hydride. The mixture was rewarmed to room temperature, and while stirring vigorously, 1 ml water, then 1 ml aqueous NaOH solution, then some THF (to thin out the mixture), and finally 3 ml water were added. The mixture was filtered, washing the filter cake with 5% MeOH in EtOAc, and the filtrate was evaporated. The residue was flash chromatographed (25% to 45% [5% MeOH in EtOAc] in hexanes gradient) to obtain 1.05 g of nearly pure title diol (approximately 90% pure=0.95 g) as an oil. The yield of title diol was 63%.
TLC (25% [5% MeOH in EtOAc] in hexanes-anisaldehyde):
  Part C lactone: 0.64
  Title diol: 0.10

E.
2-[4-[3-(Tetrahydro-3-phenyl-3-furanyl)propyl]phenyl]ethyl alcohol thexyldimethylsilyl ether To a solution of 520 mg of nearly pure Part D diol (approximately 90% pure=470 mg, 1.00 mmol) in 8 ml CH2Cl2 stirring under argon at room temperature, was added a solution of 252 mg p-toluenesulphonyl chloride (1.3 mmol, 1.3 equiv) in 5 ml CH2Cl2 dropwise over 30 minutes. TLC showed reaction was slow, and complete disappearance of starting material was not attained after stirring overnight. An additional 101 mg p-toluenesulphonyl chloride (0.5 mmol, 0.5 equiv) was added as the solid. After stirring for another day, TLC showed complete reaction (all starting material gone and very little putative tosylate intermediates), and the mixture was evaporated. Flash chromatography (10% EtOAc in hexanes) gave 460 mg of impure title tetrahydrofuran (86% pure=396 mg of title tetrahydrofuran contaminated with p-toluenesulphonyl chloride) as an oil. The yield of title tetrahydrofuran was 88%.
TLC (25% [5% MeOH in EtOAc] in hexanes-anisaldehyde):
  Part D diol 0.10
  Title tetrahydrofuran 0.71

F.
4-[3-(Tetrahydro-3-phenyl-3-furanyl)-propyl]benzeneacetic acid

To a solution of 460 mg of impure Part E tetrahydrofuran (86% pure=396 mg of Part C tetrahydrofuran, 0.88 mmol, contaminated with p-toluenesulphonyl chloride) in 25 ml acetone under argon at 0°, was added 2 ml Jones Reagent. This mixture was stirred for 30 min before 2-propanol was added to quench excess reagent.

Still at 0°, 3 M aqueous NaHSO$_3$ solution and brine were added. Extraction (3 times) with EtOAc followed. After drying the extracts over Na$_2$SO$_4$, solvent evaporation and flash chromatography (25% [2% AcOH in EtOAc]in hexanes) afforded, after azeotropic removal of AcOH by repeated rotoevaporation with CHCl$_3$ and toluene followed by exposure to high vacuum, 260 mg of nearly pure title compound (approximately 90% pure =234 mg of product, contaminated with the benzoic acid lower homologue). The product was obtained in 82% yield. This material was carefully rechromatographed (25% [5% AcOH in EtOAc]in hexanes) to obtained pure title compound.

TLC (50% [2% AcOH in EtOAc] in hexanes-anisaldehyde):
 Part E tetrahydrofuran: 0.93
 Title compound: 0.41
$^{13}$C NMR (67.8 MHz in CDCl$_3$):
 177.2, 144.9, 141.1, 130.7, 129.2, 128.5,
 128.2, 126.7, 126.1, 76.8, 67.1, 50.9, 40.6,
 39.5, 37.2, 35.7, 26.9

EXAMPLE 2

4-3-[Tetrahydro-3-(p-chlorophenyl)-3-furanyl]propyl]-benzeneacetic acid

A. α-(p-Chlorophenyl)-γ-butyrolactone

A 1M solution of lithium bis(trimethylsilyl)amide (230 ml, 0.23 mol) in THF was diluted with 60 ml of dry THF. To this was added a solution of 33.1 g of p-chlorobenzyl cyanide (0.22 mol) in 50 ml of THF. During the addition a white precipitate formed. The reaction mixture was diluted with an additional 120 ml of THF. The cold bath was removed and the reaction mixture was allowed to warm to −25° C. After stirring at −25° C. for 30 minutes, the reaction mixture was recooled to −40° C. and 30 ml of ethylene oxide (0.6 mol) was added. The cold bath was removed and the mixture was stirred at 23° C. overnight. The reaction was then quenched by the addition of 15 ml of acetic acid and concentrated in vacuo. The residue was partitioned between 200 ml each of 3 N HCl and ether. The aqueous layer was adjusted to pH=1 with 6 N HCl and extracted twice with 200 ml of ether. The combined ether layers were dried (MgSO$_4$), filtered and concentrated in vacuo to afford 46.0 g of cyano-alcohol.

To a 0° C. solution of 8.0 g of crude cyano-alcohol in 100 ml of methanol was bubbled HCl. After the exotherm subsided (pot temperature exceeded 25° C.) 20 ml of water was added and the solution was concentrated in vacuo. The residue was diluted with 100 ml of water and 200 ml of ether and stirred vigorously for 1 hour. The aqueous layer was extracted with 200 ml EtOAc, saturated with NaCl, and extracted with 200 ml of CHCl$_3$. All organics were combined, dried (MgSO$_4$), filtered and concentrated in vacuo. Chromatography on 150 g silica gel using 1:1 hexane-ether as eluent afforded 3.8% g of desired lactone.

B.
2-(4-Chlorophenyl)-2-[3-[4-[2-(thexyldimethylsilyloxy)ethyl]phenyl]propyl]-γ-butyrolactone To a solution of 1.00 g (5.1 mmol) of Part A α-(p-chlorophenyl)-γ-butyrolactone in 10 ml dry THF stirring under argon at −78° was added dropwise 6.1 ml of 1.0M lithium bis(trimethylsilyl)amide in THF solution (6.1 mmol, 1.2 equiv). A precipitate formed after 5 minutes. After stirring 1 hour, a solution of 2.2 g Example 1 Part B iodide (5.1 mmol, 1.0 equiv) in 3 ml dry THF was added dropwise. After 1 hour of stirring at −78° in the dark, the mixture was allowed to slowly warm to room temperature. All precipitate dissolved. Stirring was continued at room temperature overnight. Addition of 1 ml saturated aqueous NH$_4$Cl solution caused precipitation. The precipitate was filtered off, washing with THF, and the filtrate was concentrated. The residue was flash chromatographed (0% to 15% EtOAc in hexanes gradient) to obtain 1.85 g of pure title alkylation product as an oil. The yield of title product was 72%.

TLC (15% EtOAc in hexanes - I$_2$, UVS):
 Example 1 Part B iodide: 0.76
 α-(p-chlorophenyl)-γ-butyrolactone: 0.07
 Title lactone: 0.28

C. 3-Hydroxymethyl-3-(4-chlorophenyl)-6-[4-[2-(thexyldimethylsilyloxy)ethyl]phenyl]hexan-1-ol To a solution of 1.85 g of Part B alkylation product (3.7 mmol) in 20 ml dry Et$_2$O stirring under argon at 0°, was added 1.2 g lithium aluminum hydride (32 mmol, 8.5 equiv). The mixture was then warmed to room temperature and stirred for 1 hour. After recooling to 0°, 20% ethyl acetate in ethyl ether was cautiously added to quench excess hydride. The mixture was rewarmed to room temperature, and while stirring vigorously, 1 ml water, then 1 ml 15% aqueous NaOH solution, and finally 3 ml water were added. The mixture was filtered, washing the filter cake with 5% MeOH in EtOAc, and the filtrate was evaporated to obtain 1.88 g of crude, nearly pure title diol as an oil. This material was taken on without purification.

TLC (25% [5% MeOH in EtOAc] in hexanes-anisaldehyde):
 Part B alkylation product 0.46
 Title diol 0.07

D.
2-[4-[3-(Tetrahydro-3-(4-chlorophenyl)-3-furanyl)-propyl]phenyl]ethyl alcohol thexyldimethylsilyl ether To a solution of 1.88 g of crude, nearly pure Part C. diol in 25 ml CH$_2$Cl$_2$ plus 6 ml triethylamine stirring under argon at room temperature, was added 1.9 g p-toluenesulphonyl chloride (10 mmol, approximately 2.7 equiv). After stirring for 2 days, the mixture was evaporated. Flash chromatography (6% EtOAc in hexanes) gave 1.35 g of nearly pure title tetrahydrofuran (90% pure =1.22 g of title tetrahydrofuran, contaminated with p-toluenesulphonyl chloride) as an oil. The yield of title tetrahydrofuran was 68% overall from Part B alkylation product.

TLC (25% [5% MeOH in EtOAc]in hexanes-anisaldehyde):
 Part C diol: 0.07
 Title tetrahydrofuran: 0.60

E. 4-[3-[Tetrahydro-3-(p-chlorophenyl)-3-furanyl]propyl]-benzeneacetic acid

To a solution of 1.34 g of nearly pure Part D tetrahydrofuran (90% pure=1.21 g of Part D tetrahydrofuran, 2.48 mmol, contaminated with p-toluenesulphonyl chloride) in 25 ml acetone under argon at 0°, was added 4 ml Jones Reagent. This mixture was stirred for 30 minutes before 2-propanol was added to quench excess reagent. Still at 0°, 3 M aqueous NaHSO$_3$ solution and brine were added. Extraction (3 times) with EtOAc followed. After drying the extracts over Na$_2$SO$_4$, solvent evaporation and flash chromatography (15% [5% AcOH in EtOAc] in hexanes) afforded, after azeotropic removal of AcOH by repeated rotoevaporation with CHCl$_3$ and toluene followed by exposure to high vacuum, 686 mg of pure title product as an oil. The product was obtained in 77% yield.

TLC. 40% [5% AcOH in EtOAc] in hexanes-anisaldehyde):
  Part D tetrahydrofuran: 0.75
  Title product: 0.25
—C. NMR (67.8 MHz in CDCl$_3$):
177.0, 143.3, 140.8. 131.9. 130.8. 129.1,
128.4, 128.3, 128.0. 76.6, 67.0, 50.5, 40.5,
39.2, 37.3, 35.6, 26.8.

EXAMPLE 3

5-[2-[4-[3-(Tetrahydro-3-phenyl-3-furanyl)propyl]phenyl]ethyl]-1H-tetrazole

A. 2-[4-[3-(Tetrahydro-2-phenyl-2-furanyl)propyl]phenyl]ethyl alcohol

To a stirred solution of Example I Part E silyl ether (1.0 mmol) in 5 ml of tetrahydrofuran at 0° C. under argon is added 2.0 ml of 1M Bu$_4$NF solution. The resulting solution is stirred for minutes, then concentrated in vacuo and chromatographed on silica gel using 2% CH$_3$OH/CH$_2$Cl$_2$ as eluant to afford title compound.

B. 2-[4-[3-Tetrahydro-3-phenyl-3-furanyl)propyl]phenyl]ethyl bromide

To a 0° C. solution of 1 mmol of triphenylphosphine in 5 ml of toluene is added dropwise 1 mmol of bromine. The resulting slurry is stirred for 30 minutes at 0° C. and then a solution of title A alcohol and 1 mmol of pyridine in 1 ml of toluene is added. The mixture is stirred at 0°–10° C. for 3 hours and the partitioned between saturated aqueous NaHCO$_3$ and ether. The aqueous layer is extracted with ether and combined ether layers are dried (MgSO$_4$), filtered and concentrated in vacuo. The residue is triturated in cold hexane, filtered to remove triphenyl phosphine oxide, and concentrated in vacuo to give title B bromide.

C. 3-[4-[3-(Tetrahydro-3-phenyl-3-furanyl)propyl]phenyl]-propionitrile

To a solution of 1 mmol title B bromide in 4 ml DMSO and 1 ml of THF is added 5 mmol of sodium cyanide. This is heated to 90°–95° C. for 4 hours, cooled and partitioned between 40 ml each of water and ether. Aqueous layer is extracted with ether. Combined ether layers are washed with water, dried over MgSO$_4$, filtered and concentrated in vacuo. Purification is effected by chromatography on silica gel using hexane-CH$_2$Cl$_2$ mixtures as eluant to give title C nitrile.

D. 5-[2-[4-[3-(Tetrahydro-3-phenyl-3-furanyl)propyl]phenyl]ethyl]-1H-tetrazole To a stirred solution of 1 mmol title C nitrile in 5 ml of DMF is added 6 mmol of sodium azide and 6 mmol of ammonium chloride. This mixture is heated at 120° C. for 24 hours under argon. On cooling, the reaction mixture is concentrated in vacuo to remove most of the DMF. The residue is partitioned between CHCl$_3$ and dilute (0.1–0.5 N) HCl. The CHCl$_3$ layer is dried over MgSO$_4$, filtered and concentrated in vacuo to afford the crude tetrazole. Purification is effected using CH$_3$OH (2–4%) in CH$_2$Cl$_2$ as eluant to afford title compound.

EXAMPLE 4

N-Phenylsulfonyl-4-[3-(tetrahydro-3-phenyl-3furanyl)-propylbenzene acetamide

To a 0° C. solution of 1 mmol of Example 1 acid in 5 ml of THF is added 1 mmol of 1,1'-carbonyldiimidazole. This is stirred for 2 hours at 0° C. To this mixture is added 1 mmol of benzene sulfonamide. The mixture is stirred at 25° C. for 1 hour and then heated to reflux for 2 hours. On cooling, the reaction miture is partitioned between 1N HCl and ethyl acetate. The EtOAc layer is dried, filtered and concentrated in vacuo. Purification is effected by silica gel chromatography to give title compound.

EXAMPLES 5 to 20

Following the procedure of Examples 1 and 2 except substituting for Example 1 part A bromide the bromoalkyl benzene compound shown in Column II of Table I set out below and substituting for the Example 1 Part C lactone, the lactone shown in Column I, the product shown in Column III is obtained.

TABLE I

| Ex. No. | n | Column I $Z$-(CH$_2$)$_n$ lactone | | Column II Br—(CH$_2$)$_p$—phenyl—(CH$_2$)$_q$—CH$_2$—Pro | | | Column III |
|---|---|---|---|---|---|---|---|
| | | Z | (CH$_2$)$_p$ | phenyl positions 1,2,3,4 | (position)-(CH$_2$)$_q$— | | |
| 5. | 1 | phenyl | —CH$_2$—CH(CH$_3$)— | | (4)- | —CH$_2$—(CH$_2$)$_2$— | Same as Col. I; Same as Col. II |
| 6. | 2 | naphthyl | —CH$_2$—CH$_2$— | | (3)- | —CH$_2$—CH$_2$CH$_2$—CH$_2$— | |
| 7. | 1 | 4-F-phenyl | —CH$_2$—C(H)(CH$_3$)—C(CH$_3$)— | | (2)- | —CH(CH$_3$)—CH$_2$— | |
| 8. | 2 | 4-HO-phenyl | —CH(C$_2$H$_5$)—CH$_2$— | | (4)- | —CH$_2$—CH$_2$— | |
| 9. | 1 | 4-CH$_3$O-phenyl | —CH$_2$—CH$_2$—CH(CH$_3$)—CH$_2$— | | (4)- | —CH$_2$— | |
| 10. | 2 | phenyl | —CH(CH$_3$)—CH(CH$_3$)— | | (3)- | —CH$_2$—CH(CH$_3$)—CH$_2$— | |
| 11. | 1 | biphenyl | —CH(CH$_3$)—CH(OCH$_3$)— | | (2)- | —CH$_2$—C(CH$_3$)$_2$—CH$_2$— | |

TABLE I-continued

| | Column I | | Column II | | Column III | | |
|---|---|---|---|---|---|---|---|
| | ![structure with Z, (CH$_2$)$_n$, O] | | Br—(CH$_2$)$_p$—[ring 1,2,3,4]—(CH$_2$)$_q$—CH$_2$—Pro | | ![structure with Z, (CH$_2$)$_n$, O, (CH$_2$)$_p$—ring—(CH$_2$)$_q$—COOH] | | |
| Ex. No. | n | Z | (CH$_2$)$_p$ | (position)-(CH$_2$)$_q$— | n | Z | (position)-(CH$_2$)$_p$—ring—(CH$_2$)$_q$— |
| 12. | 2 | ![phenyl] | —(CH$_2$)$_3$— | (4)- —CH$_2$—CH—CH—CH$_2$— with CH$_3$ CH$_3$ | | | |
| 13. | 1 | ![biphenyl-OCH$_3$] | —CH$_2$—CH—CH—CH$_2$— with CH$_3$ CH$_3$ | (3)- —CH—CH$_2$— with C$_2$H$_5$ | | | |
| 14. | 2 | ![CH$_3$—NH—phenyl] | CH$_2$CH$_2$ | (4)- —CH—CH— with OCH$_3$ OCH$_3$ | | | |
| 15. | 1 | ![C$_3$H$_7$—phenyl] | CH$_2$CH$_2$ | (3)- —CH— with OCH$_3$ | | | |
| 16. | 2 | ![C$_2$H$_5$NH—phenyl] | CH$_2$—CH$_2$ | (2)- —CH$_2$CH$_2$— | | | |
| 17. | 1 | ![(CH$_3$)$_3$C—phenyl] | —CH$_2$—CH— with CH$_3$ | (4)- CH$_2$—(CH$_2$)$_2$— | | | |
| 18. | 2 | ![HO—phenyl] | —CH$_2$—CH$_2$— | (3)- —CH$_2$—CH$_2$CH$_2$—CH$_2$— | | | |

TABLE I-continued

| | Column I | | Column II | | | Column III | | |
|---|---|---|---|---|---|---|---|---|
| Ex. No. | structure | n | structure | (position)-(CH$_2$)$_q$— | | structure | n | (position)-(CH$_2$)$_p$— |
| 19. | | 1 | | (2)- —CHCH$_2$— with CH$_3$ above; —CH$_2$—C(H)(CH$_3$)—CH$_2$— | | | | |
| 20. | | 2 | | (4)- —CH$_2$—CH$_2$—; —CH$_2$—CH(C$_2$H$_5$)— | | | | |

EXAMPLES 21 to 32

Following the procedures of Example 1 parts A through E and Example 3 except substituting for the Example 1 Part A bromide, the bromoalkyl benzene compound shown in Column II of Table II set out below and substituting for the Example 1 Part C lactone, the lactone shown in Column I, the product shown in Column III is obtained.

TABLE II

Column I structure: lactone with $(CH_2)_n$ ring containing Z substituent, O, and C=O.

Column II structure: $Br-(CH_2)_p-$ phenyl (positions 1,2,3,4) $-(CH_2)_q-Pro$

| Ex. No. | n | Z | $(CH_2)_p$ | (position)-$(CH_2)_q$- |
|---|---|---|---|---|
| 21. | 1 | phenyl | $-CH_2-CH(CH_3)-$ | (4)- $CH_2-(CH_2)_2-$ |
| 22. | 2 | 2-naphthyl | $-CH_2-CH_2-$ | (3)- $-CH_2-CH_2CH_2-CH_2-$ |
| 23. | 1 | 4-fluorophenyl | $-CH_2-C(H)(CH_3)-CH(CH_3)-$ | (2)- $-CH(CH_3)-CH_2-$ |
| 24. | 2 | 4-chlorophenyl | $-CH(C_2H_5)-CH_2$ | (4)- $-CH_2-CH_2-$ |
| 25. | 1 | 4-methoxyphenyl | $-CH_2-CH_2-CH(CH_3)-CH_2-$ | (4)- $-CH_2-$ |
| 26. | 2 | phenyl | $-CH(CH_3)-CH(CH_3)-$ | (3) $-CH_2-CH(CH_3)-CH_2-$ |
| 27. | 1 | 4-methylphenyl | $-CH(CH_3)-CH(OCH_3)-$ | (2)- $-C(CH_3)_2-CH_2CH_2-$ |
| 28. | 2 | 4-hydroxyphenyl | $-(CH_2)_3-$ | (4)- $-CH_2-CH(CH_3)-CH(CH_3)-CH_2-$ |
| 29. | 1 | 4-methoxybiphenyl | $-CH_2-CH(CH_3)-CH(CH_3)-$ | (3)- $-CH(C_2H_5)-CH_2-$ |
| 30. | 2 | 4-ethylphenyl | $-CH_2CH_2-$ | (4)- $-CH(OCH_3)-CH(H)-$ |
| 31. | 1 | 4-propylphenyl | $-(CH_2)_3-$ | (3)- $-CH(OCH_3)-CH_2CH_2-$ |

TABLE II-continued

| Ex. No. | n | (structure) | | (position)-(CH₂)q— |
|---|---|---|---|---|
| 32. | 2 | 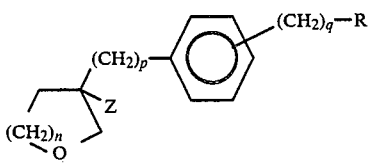 | $CH_2$—$CH_2$ | (2)- —$CH_2CH_2$— |

Column III

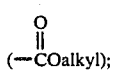

| Ex. No. | n | Z | (CH₂)p | (position)-(CH₂)q— |
|---|---|---|---|---|
| 21. | | Same as | | Same as Col. II |
| 22. | | Col. I | | |
| 23. | | | | |
| 24. | | | | |
| 25. | | | | |
| 26. | | | | |
| 27. | | | | |
| 28. | | | | |
| 29. | | | | |
| 30. | | | | |
| 31. | | | | |
| 32. | | | | |

EXAMPLES 33 to 48

Following the procedure of Example 4 using as a starting material the acids of Examples 5 to 20, the corresponding sulfonamides are obtained.

What is claimed is:

1. A compound of the structure

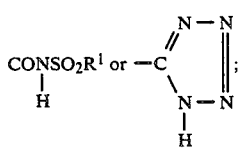

wherein

Z is aryl, which may be optionally substituted with one or more of halo, lower alkyl, lower alkoxy, hydroxy, lower alkylamino, phenyl or carbo-lower alkoxy $$\underset{H}{-\overset{O}{\overset{\|}{C}}\text{alkyl}};$$

R is COOH, COO alkali metal, COO lower alkyl, $$\underset{H}{\overset{|}{CONSO_2R^1}} \text{ or } -\underset{\underset{H}{\overset{|}{N-N}}}{\overset{N-N}{\overset{\|}{C}}};$$

$R^1$ is lower alkyl or aryl;
n is 1 or 2;
p is 2 to 5; and
q is 1 to 4;
and the $(CH_2)_n$, $(CH_2)_p$ and/or $(CH_2)_q$ groups may be unsubstituted or substituted with one or two lower alkyl groups and/or are one or two lower alkoxy groups.

2. The compound as defined in claim 1 wherein n is 1.

3. The compound as defined in claim 1 wherein n is 2.

4. The compound as defined in claim 1 wherein n is 1, $(CH_2)_p$ is $(CH_2)_3$, $(CH_2)_q$ is $CH_2$, —$(CH_2)_q$—R is in the para position, Z is aryl and R is COOH.

5. The compound as defined in claim 4 wherein —$(CH_2)_q$—R— is in the 4-position.

6. The compound as defined in claim 1 having the name 4-[3-(tetrahydro-3-phenyl-3-furanyl)propyl]benzeneacetic acid.

7. The compound as defined in claim 1 having the name methyl 4-[3-[tetrahydro-3-(4-chlorophenyl)phenyl-3-furanyl]propyl]benzeneacetic acid.

8. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

9. The method as defined in claim 8 wherein said compound is administered in an amount within the range of from about 0.1 to about 100 mg/kg.

10. A composition for inhibiting arachidonic acid-induced platelet aggregation and bronchoconstriction comprising an effective amount of a compound as defined in claim 1 or a pharmaceutially acceptable salt thereof, and a pharmaceutically acceptable carrier therefor.

11. A method of inhibiting platelet aggregation which comprises administering to a mammalian host an effective amount of a compound as defined in claim 1 or a pharmaceutically acceptable salt thereof.

12. A method of inhibiting bronchoconstriction associated with asthma, which comprises administering to a mammalian host an effective amount of a compound as defined in claim 1 or a pharmaceutically acceptable salt thereof.

13. A method of treating peripheral vascular diseases, which comprises topically or systemically administering to a mammalian host an effective amount of a compound as defined in claim 1 or a pharmaceutically acceptable salt thereof.

* * * * *